United States Patent [19]

Stehling

[11] Patent Number: 5,008,204
[45] Date of Patent: Apr. 16, 1991

[54] METHOD FOR DETERMINING THE COMPOSITIONAL DISTRIBUTION OF A CRYSTALLINE COPOLYMER

[75] Inventor: Ferdinand C. Stehling, Baytown, Tex.

[73] Assignee: Exxon Chemical Patents Inc., Linden, N.J.

[21] Appl. No.: 151,350

[22] Filed: Feb. 2, 1988

[51] Int. Cl.$^5$ ............... G01N 25/00; G01N 30/02; G01N 31/02; G01N 33/44
[52] U.S. Cl. .................................. 436/85; 73/53; 73/61.1 C; 210/656; 210/774; 436/161
[58] Field of Search ............... 436/85, 161; 73/53, 73/61.1 C; 210/-35, 656, 774, 198.2, 662; 528/481; 422/70

[56] References Cited

U.S. PATENT DOCUMENTS 3,963,799  6/1976  Starkweather, Jr. ............ 525/183
4,515,992  5/1982  Gupta ............................... 428/380
4,798,081  1/1989  Hazlitt et al. ..................... 73/61.1 C

OTHER PUBLICATIONS

Hosoda, "Structural Distribution of Linear Low-Density Polyethylenes", *Polymer Journal*, vol 20, No. 5, pp. 383–397.
Kalin et al., "Long and Short Chain Branching Frequency in Low Density Polyethylene" *Pure & Applied Chemistry*, vol. 60, No. 9, pp. 1403–1415.
L. Wild, T. R. Ryle, D. C. Knobeloch and I. R. Peat, "Determination of Branching Distributions in Polyethylene and Ethylene Copolymers, Journal of Polymer Science": Polymer Physics Ed., vol. 20, 441–455.
C. Bergstrom, E. Avela, "Investigation of the Composite Molecular Structure of LDPE by Using Temperature Rising Elution Fractionation", Journal of Applied Polymer Science, vol. 23, 163–171.
S. Nakano, Y. Goto, "Development of automatic Cross Fractionation: Combination of Crystallizability Fractionation and Molecular Weight Fractionation", Journal of Applied Polymer Science, vol. 26, pp. 4217–4231.

*Primary Examiner*—Robert J. Hill, Jr.
*Attorney, Agent, or Firm*—M. B. Kurtzman

[57] ABSTRACT

A method for fractionating crystalline copolymers to determine solubility distribution as a function of temperature. Fractionation is conducted by passing a solvent through a column containing the crystallized copolymer at an increasing temperature from 6° C. to about 120° C. The polymer solution exiting the column is analyzed by infrared spectroscopy or NMR to determine the composition distribution of the copolymer.

11 Claims, 3 Drawing Sheets

METHOD FOR DETERMINING THE COMPOSITIONAL DISTRIBUTION OF A CRYSTALLINE COPOLYMER

FIELD OF THE INVENTION

The present invention relates to the solvent fractionation of a polymer. More specifically, the invention relates to the fractionation of a copolymer with a single solvent at different temperatures.

BACKGROUND

Crystalline copolymers, such as linear low density polyethylene (LLDPE) and ethylene vinyl acetate (EVA), are known to have molecular weight distributions and composition distributions. The properties of copolymers having similar average compositions can vary considerably depending upon the compositional distribution of the copolymer. For example, in co-pending application serial number 944,385 filed 12/19/B6 which is incorporated herein by reference, it was established that the molecular weight distribution for Exxon LL3001 linear low density polyethylene resin was narrower than the molecular weight distribution of another commercially available linear low density polyethylene. Compositional distributions are known to have a strong effect on the physical properties of copolymers, e.g., heat sealing, tear strength, and FDA extraction limits.

The molecular weight and compositional distributions of copolymers have been determined by solvent fractionation of the crystalline copolymer and analysis of the fractions for molecular weight and composition. Apparatus for solvent fractionating of copolymers are known in the art. Such apparatus typically operate by dissolving the copolymer in a hot solvent and allowing the solvent to cool to ambient temperature within a packed column. The copolymer crystallizes on the column packing as the polymer cools. It is known in the art to cool the polymer to slightly above ambient temperature, about 30° C, before starting fractionation with pure solvent.

Fractionation of the crystallized polymer is typically conducted with a single solvent that is passed through the column at increasing column temperatures beginning at the lowest temperature obtained during cooling of the copolymer. Less soluble fractions of the copolymer are dissolved and removed from the column as the column temperature rises such that the solvent effluent from the column containing dissolved copolymer can be collected in consecutive fractions which are identified by a starting and ending column temperature. These fractions are then analyzed for molecular weight distribution and monomer composition by conventional means.

SUMMARY OF THE INVENTION

The present invention is a method for determining the compositional distributions of a crystalline copolymer comprising the steps of dissolving the copolymer in a solvent at elevated temperature, filling a column with the solvent containing the dissolved copolymer, crystallizing the copolymer within the column by reducing the temperature of the column to below ambient temperature, e.g. to temperatures at least about 6° C or lower, initially passing pure solvent through the column at a constant temperature below ambient to determine the amount of uncrystallized copolymer, and then at increasing temperature to gradually dissolve the copolymer, continuously measuring the concentration of the copolymer in the solvent exiting the column. The method is preferably conducted with a fractionation temperature range of from 0 to 120° C and with tetrachloroethylene as the solvent. The effluent from the fractionation column is preferably continuously analyzed by an IR detector to determine the concentration of polymer in the solvent.

DETAILED DESCRIPTION OF A PREFERRED EMBODIMENT

Figure 1:
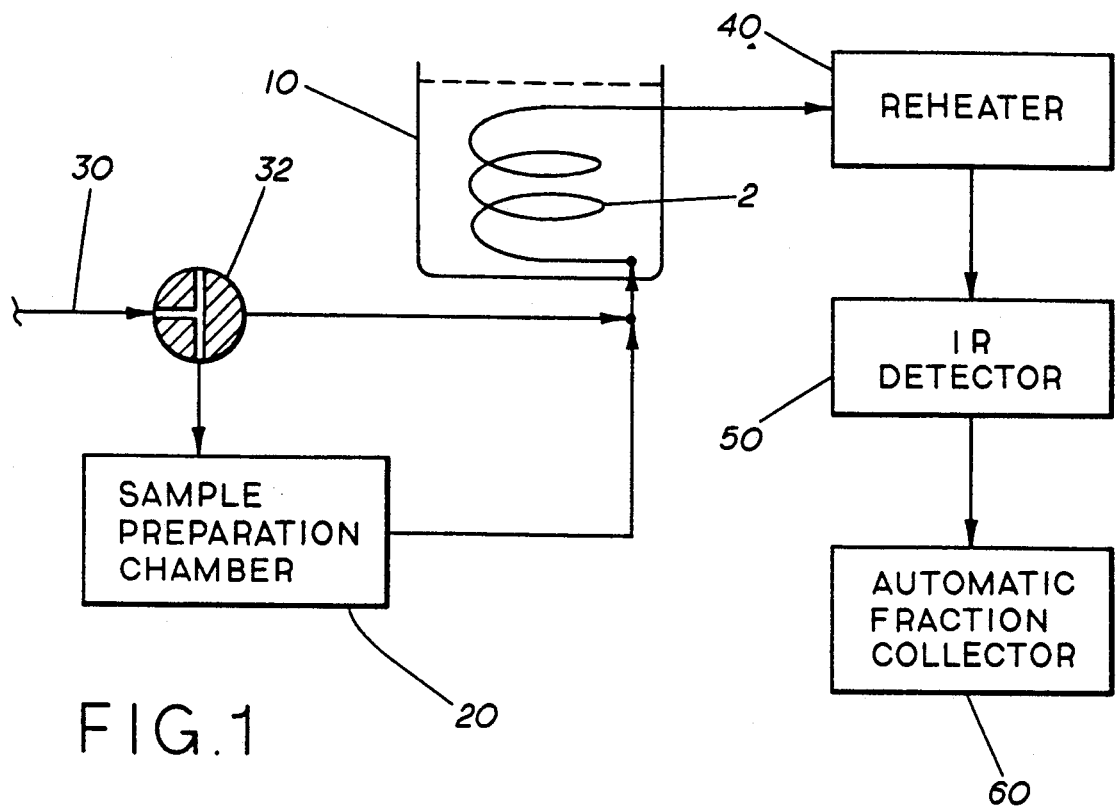
FIG. 1 is a schematic diagram of the sample preparation mode for an apparatus which can determine the solubility distribution curve of a crystalline polymer in accordance with the method of the present invention.

The method of the present invention has been practiced with an apparatus that automatically determines the solubility distribution curve of a crystalline copolymer. Referring to FIG. 1, a steel column is packed with glass beads (approximately 35 mesh) and immersed in an oil bath 10. A column having an inside diameter of 35 mm and a length of 400 mm has worked well. The temperature of the oil bath can be programmed over any desirable temperature range, e.g. from below ambient, preferably about or below 6 C, or about or below −12° C, although even lower temperatures may be employed, to a temperature up to about 150 C. Solvent used in the fractionation may be prevented from boiling by operating the apparatus at about 3 atmospheres pressure. A weighed amount of sample, usually about 1.6 grams, is placed in a sample preparation chamber 20, that is then sealed and repeatedly evacuated and filled with argon. A metered volume of solvent 30, preferably tetrachloroethylene, is then pumped through a three-way valve 32 into the sample preparation chamber 20 where it is stirred and heated to obtain a solution of about 1 percent concentration. A metered volume of this solution, usually about 100 cc, is then pumped into the packed column 2 which has been thermostated at a high temperature of usually at least about 120° C.

Figure 2:
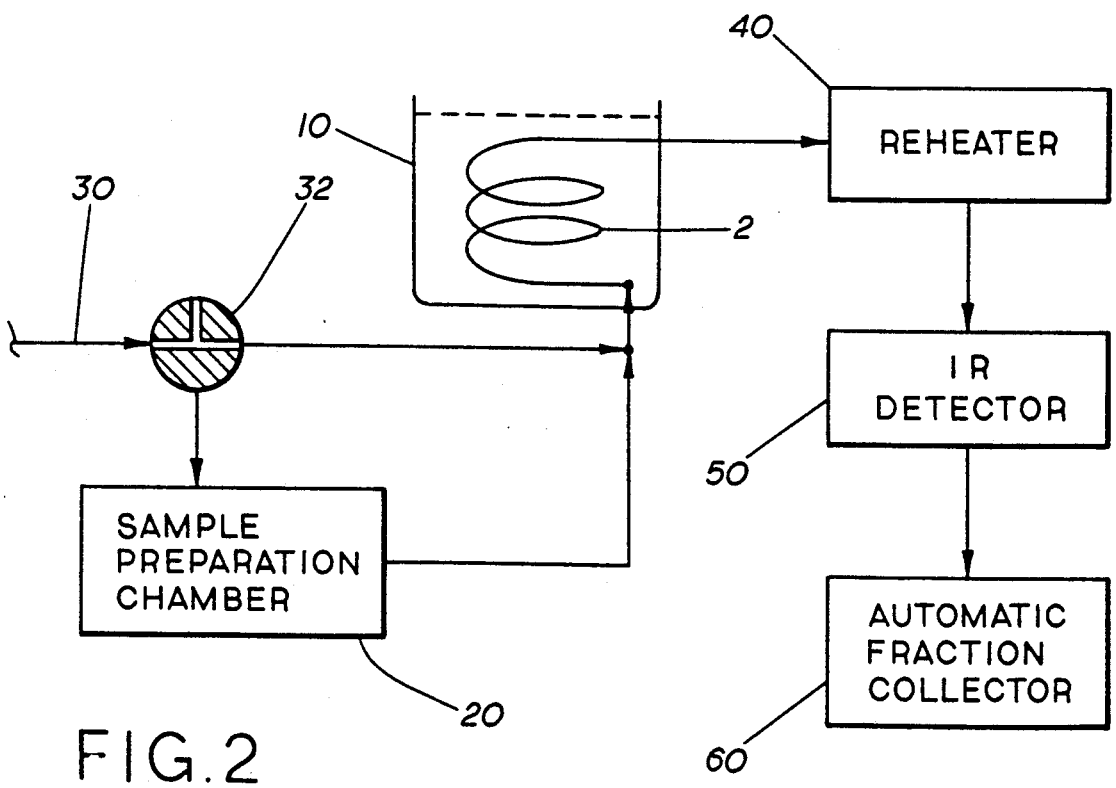
FIG. 2 shows the apparatus of FIG. 1 in the solvent fractionation mode.

The polymer solution sample is subsequently crystallized by cooling the polymer in the column 2 at a programmed rate of 5° C per hour to below ambient temperature in order to increase the proportion of the polymer crystallized, e.g., to below or about 6° C. However, some polymers may require lower crystallization temperatures, e.g. about or below −6° C or −12 C. The column 2 is then maintained at this low temperature for at least an hour. Thereafter, the elution of fractionation stage shown in FIG. 2 is started by pumping pure solvent 30 through the column 2 at the rate of 6 cc per minute. Effluent from the column 2 passes through a reheater 40 where it is heated to 120° C before passing through an IR detector 50 which is used to measure the absorbance of the effluent stream. The infrared absorbance of the polymer carbon-hydrogen stretching bands at about 2960 cm$^{-1}$ serves as a continuous measure of the relative concentration of polymer in the effluent. After passing through the infrared detector 50 the temperature of the effluent is reduced to about 110° C and the pressure is reduced to 1 atmosphere before passing the stream into an automatic fraction collection 60.

In the elution stage, the pure solvent is initially pumped through the column 2 at the low initial temperature for one hour. This serves to flush polymer that has not crystallized during the crystallization stage out of the column 2 so that the percent of uncrystallized polymer can be determined from the infrared trace. The temperature is then programmed upward at 10° C. per hour to 100° C and at 20° C per hour from 100° C to 120° C.

The compositions of fractions obtained from the various polymers are determined by infrared spectroscopy. The IR compositions are obtained from the intensity of the 1378 cm-1 methyl band, the thickness of the sample, and a calibration curve based on samples whose compositions can be determined independently H 7 by NMR. No corrections for polymer end groups is usually made in obtaining compositions from infrared data.

Example 1

An example of a solubility distribution obtained from a typical LLDPE sample, Dow 2045 [poly{ethylene-co-octene}, 0.918 g/cc, melt index 1.01 obtained using the procedure of the invention described above is shown in FIG. 3. A composition scale obtained by analysis of fractions from poly(ethylene-co-butene}, poly-{ethylene-co-hexene}and poly{ethylene-co-octene}eluted at various temperatures is also shown in FIG. 3.

Figure 3:
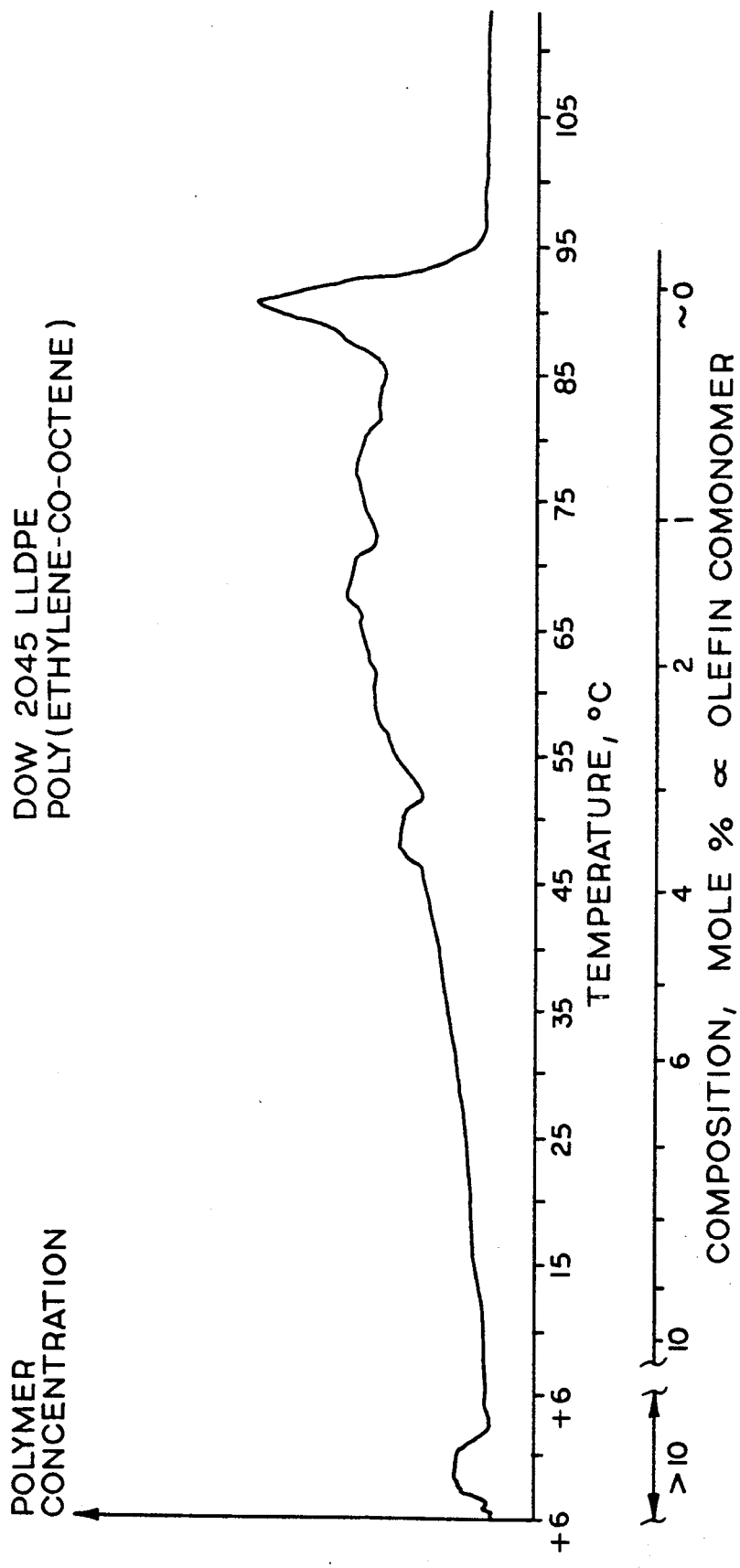
FIG. 3 is an exemplary solubility distribution curve which was generated by the method of the present invention.

As seen in FIG. 3, the solubility versus temperature distributions for the polymer has a peak for the 6° C first-hour elution temperature. This initial peak represents the fraction of total polymer that is not crystallizable at the lowest temperature of the experiment {about 6° C}. The typical run length for a sample is about 40 hours.

Example 2

Figure 4:
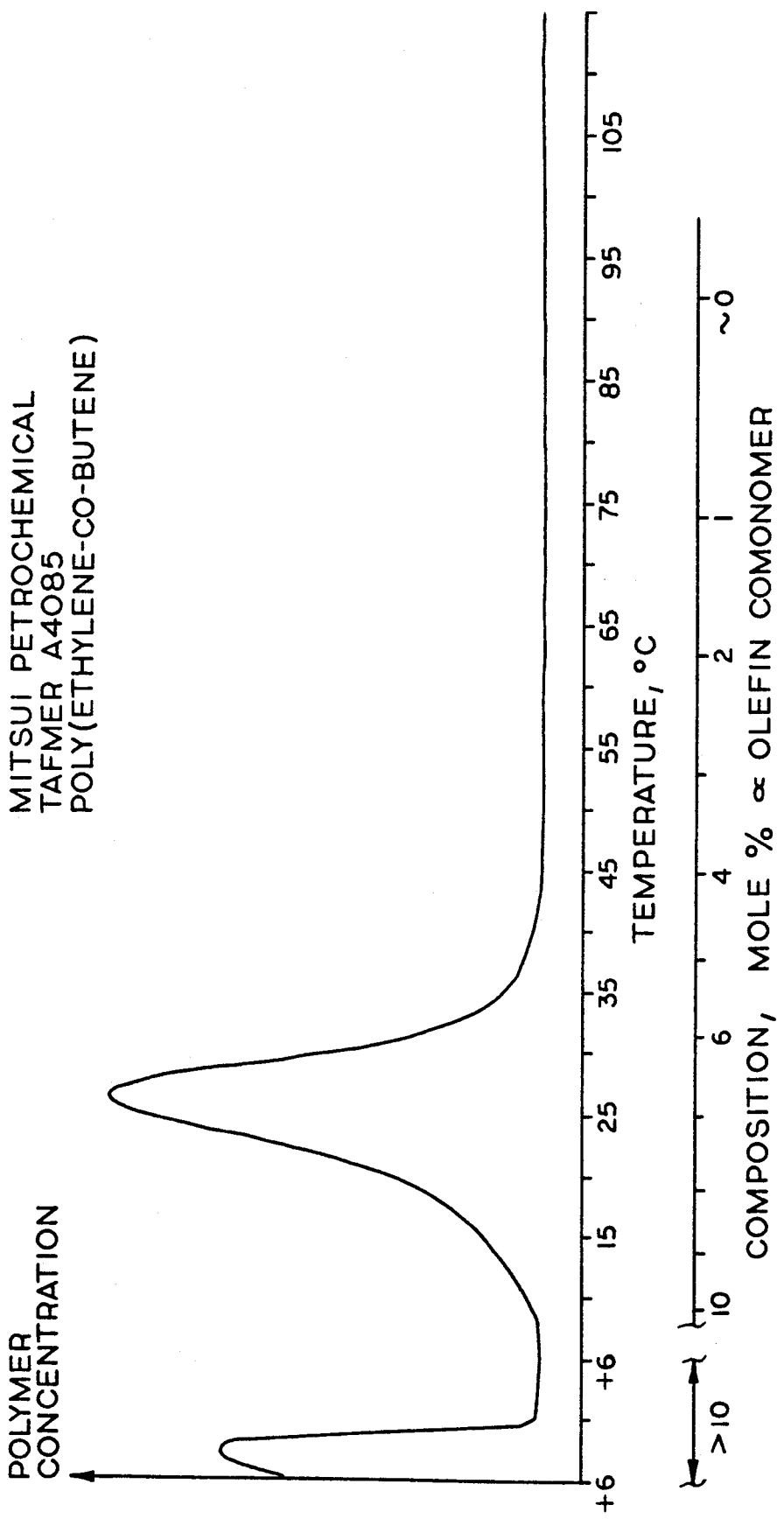
FIG. 4 is another exemplary solubility distribution curve generated by the method of the present invention.

Another example of a solubility distribution and composition distribution is shown in FIG. 4. The polymer sample was Mitsui Petrochemical Company Tafmor A4085 poly{ethylene- co-butene}, density -0.B8 g/cc, melt index 1.0. The curve was obtained according to the invention using the procedures described above. This example illustrates the importance of elution at sub-ambient temperature since only a small portion of this sample would have been resolved by elution only at 30° C and above as done in the prior art.

The apparatus and method described above provide a plot of concentration of polymer versus elution temperature. The fractions of solvent containing dissolved copolymer can then be analyzed by conventional means for molecular weight and composition to establish the molecular weight distribution and composition distribution of monomer. Alternatively to determining the monomer composition for each fraction, a calibration curve relating elution temperature to monomer composition can be generally derived for specific comonomers.

The foregoing description is illustrative and explanatory of the invention and is not intended to limit the invention to the specific embodiment that is described.

I claim:

1. A method for determining the solubility distribution of a crystalline copolymer, comprising the steps of:
    dissolving the copolymer in a solvent at elevated temperature;
    filling a column with the solvent containing the dissolved copolymer;
    crystallizing the copolymer within the column by reducing the temperature of the column to below ambient temperature;
    passing pure solvent through the column at an increasing column temperature to gradually dissolve the copolymer; and
    continuously measuring the concentration of the copolymer in the solvent exiting the column.

2. The method of claim 1, wherein the solvent is tetrachloroethylene.

3. The method of claim 1, wherein the pure solvent is passed through the column below ambient temperature to substantially remove uncrystallized polymer prior to increasing the column temperature.

4. The method of claim 1, wherein the column temperature is increased from about 6° C to about 150° C.

5. The method of claim 1, further comprising the steps of:
    collecting the solvent exiting the column in fractions; and
    analyzing the solvent fractions for molecular weight and monomer composition.

6. A method for determining the solubility distribution and composition distribution of a crystalline copolymer, comprising the steps of:
    dissolving the copolymer in a solvent at elevated temperature;
    filling a packed column with the solvent containing the dissolved copolymer;
    crystallizing the copolymer within the column by reducing the temperature of the column to below or about 6° C,
    passing pure solvent through the column at an increasing column temperature to gradually dissolve the copolymer;
    continuously measuring the concentration of the copolymer in the solvent exiting the column;
    collecting the solvent exiting the column in fractions; and
    analyzing the solvent fractions for molecular weight and monomer composition.

7. The method of claim 6, wherein the solvent is tetrachloroethylene.

8. The method of claim 6, wherein the pure solvent is passed through the column at or below about 6° C for at least one hour to remove uncrystallized polymer prior to increasing the column temperature.

9. The method of claim 6, wherein he column temperature is increased from about 6° C. to about 150° C.

10. A method for determining the solubility distribution and composition distribution of a crystalline copolymer, comprising the steps of:
    dissolving the copolymer in a solvent at elevated temperatures;
    filling a column with the solvent containing the dissolved copolymer;
    crystallizing the copolymer within the column by reducing the temperature of the column to about 0° C.,
    passing pure solvent through the column at 0° C for at least an hour to remove uncrystallized polymer;
    passing pure solvent through the column at an increasing column temperature of from about 0° C. to about 150° C. to gradually dissolve the crystallized copolymer.

continuously measuring the concentration of the copolymer in the solvent exiting the column;
collecting the solvent exiting the column in fractions; and
analyzing the solvent fractions for molecular weight and composition.

11. The method of claim 10, wherein the solvent is tetrachloroethylene.

* * * * *

UNITED STATES PATENT AND TRADEMARK OFFICE
CERTIFICATE OF CORRECTION

PATENT NO. : 5,008,204
DATED : April 16, 1991
INVENTOR(S) : Ferdinand C. Stehling It is certified that error appears in the above-indentified patent and that said Letters Patent is hereby corrected as shown below:

Column 2, line 57, please delete "-12 C" and substitute therefor -- -12° C --.

Column 3, line 21, please delete "H 7 by" and substitute therefor -- by $C^{13}$ --.

Column 3, line 46, please delete "Tafmor" and substitute therefor -- Tafmer --.

Column 3, line 47, please delete "-0.B8" and substitute therefor -- ~0.88 --.

Signed and Sealed this

Eighth Day of June, 1993

Attest:

MICHAEL K. KIRK

Attesting Officer

Acting Commissioner of Patents and Trademarks